United States Patent [19]
Stringer

[11] Patent Number: 4,589,875
[45] Date of Patent: May 20, 1986

[54] METHOD OF APPLYING A MALE INCONTINENCE DEVICE

[76] Inventor: Leonard C. Stringer, 3907 Goodnight Ave., Pueblo, Colo. 81005

[21] Appl. No.: 497,593

[22] Filed: May 24, 1983

[51] Int. Cl.⁴ ............................................. A61F 5/44
[52] U.S. Cl. ................................................. 604/351
[58] Field of Search ............... 604/326, 323, 346–351, 604/335, 343, 345; 128/760, 766, 767

[56] References Cited

U.S. PATENT DOCUMENTS

| | | | |
|---|---|---|---|
| 3,336,926 | 8/1967 | Gresham | 604/349 |
| 3,339,551 | 9/1967 | Stoutenburgh | 604/349 |
| 3,398,745 | 8/1968 | Tjerneld et al. | 604/349 |
| 4,540,409 | 10/1985 | Nystrom et al. | 604/349 |

FOREIGN PATENT DOCUMENTS

| | | | |
|---|---|---|---|
| 2010864 | 9/1971 | Fed. Rep. of Germany | 604/349 |
| 2249406 | 4/1973 | Fed. Rep. of Germany | 604/349 |

OTHER PUBLICATIONS

Catalog Cut, "Bard-McGuire Urinal", Bard Home Health Division C. R. Bard, Inc., Berkeley Heights, N.J. 07922, 12-1979.

Catalog Cut, "New Uro-San Plus Male External Catheter" Mentor Corp. 1499 West River Road North Minneapolis, Minn., 55411.

*Primary Examiner*—J. L. Kruter
*Attorney, Agent, or Firm*—Berman, Aisenberg & Platt

[57] ABSTRACT

Apparatus and method are disclosed for directing urine from an incontinent male patient to a discharge tube. The apparatus comprises a sheath made of a thin, flexible membrane and having a tapered portion and a cylindrical portion. The tapered portion engages the base of the patient's penis and the cylindrical portion is folded over the tapered portion to provide additional sealing force and to extend outwardly to form a surge chamber. According to the disclosed method, the tapered portion is first moved over the glans penis to a position on the base of the penis. The cylindrical portion is then folded over the tapered portion to provide the surge chamber.

4 Claims, 5 Drawing Figures

METHOD OF APPLYING A MALE INCONTINENCE DEVICE

FIELD OF THE INVENTION

This invention relates to the art of incontinence devices for male patients wherein urine from the patient is directed to a discharge tube for disposal.

BACKGROUND ART

Devices used for incontinent male patients are known. One such device is a catheter wherein a tube is inserted into the penis so that urine is passed through the tube and into a collection device. The known catheter is very painful, particularly if the patient is incontinent for a substantial period of time. For example, a patient with a catheter may suffer substantial pain from bladder spasms and cramps which cannot be corrected by the use of prescription drugs.

Devices which attach to the exterior of the penis are also known. U.S. Pat. Nos. 3,511,241 (Lee); 3,742,953 (Lee); 3,749,096 (Donaldson); 3,835,857 (Rogers, III et al.); 3,916,902 (Lineberger); and 3,999,550 (Martin) show incontinence devices for male patients wherein a bag encircles the penis and wherein one end of the bag is connected to a tube for disposal of the urine. Each of these devices requires a clumsy mechanism, usually a collar or cuff, for sealing the bag to the penis and several of them require truss-like arrangements for supporting the bags. These devices are all quite awkard to use and are not useful for certain types of patients. For example, an extremely obese patient may have great difficulty in using such a device because the lower abdomen is so large that it interferes with the bulky prior art devices. Clearly, the use of a truss-like arrangement to secure the bag is extremely impractical with this type of patient.

U.S. Pat. No. 4,198,979 (Cooney, et al.) shows a urine collector for women. This is simply a funnel-shaped apparatus which is secured over the urethral orifice to direct the urine to a discharge tube.

British Patent No. 667,012 (J. D. Franklin & Sons, Ltd.) shows a device for a male patient wherein a penis-receiving member is attached to a receiver for carrying the urine to a bowl. This device must be secured to the patient by straps similar to a truss.

SUMMARY OF THE INVENTION

Applicant's invention is an apparatus including a sheath made of an extremely thin, flexible material having a frustoconical, or tapered, portion and a tubular, substantially cylindrical portion. The frustoconical portion is applied to the penis by first lubricating the glans penis and then forcing the frustoconical portion over the glans penis and onto the base of the penis. This provides a true seal because of the elasticity of the thin sheath. The cylindrical portion is then folded over the frustoconical portion to provide a tube extending outwardly from the patient. This tube is then connected to a funnel which has a discharge tube for directing the urine to a container.

The sheath is preferably initially rolled so that the application is easily performed by simply applying the frustoconical portion and then unrolling the cylindrical portion. The frustoconical portion may be adjusted in size by trimming the end to obtain a selected diameter.

The method of the invention includes applying the frustoconical portion to the base of the penis by sliding it over the glans penis and then unrolling the cylindrical portion of the sheath.

The invention has been shown to be very useful since it is virtually painless and may remain in place for a long period of time. Also, since the thin, flexible membrane is inexpensive, it may be discarded daily without significant cost. This means that the patient may be bathed and a new apparatus applied each day without discomfort or large expense. The invention is quite useful for a wide variety of patients since it is easily applied and is not objectionable physically. For example, an obese patient who cannot utilize a catheter or prior art incontinence device may quite easily utilize the device according to the invention because of the extremely thin, flexible nature of the sheath coupled with the very efficient liquid-tight seal which does not require a collar or cuff.

It is an object of this invention to provide an apparatus for directing urine from an incontinent patient to a disposal container.

It is an object of this invention to provide a device useful for an incontinent patient, wherein the device is made of an extremely thin, flexible material which requires no additional means for obtaining a liquid-tight seal.

It is an object of this invention to provide a method for the application of a device having a frustoconical portion and a cylindrical portion to an incontinent patient.

DETAILED DESCRIPTION OF THE INVENTION

Figure 1:
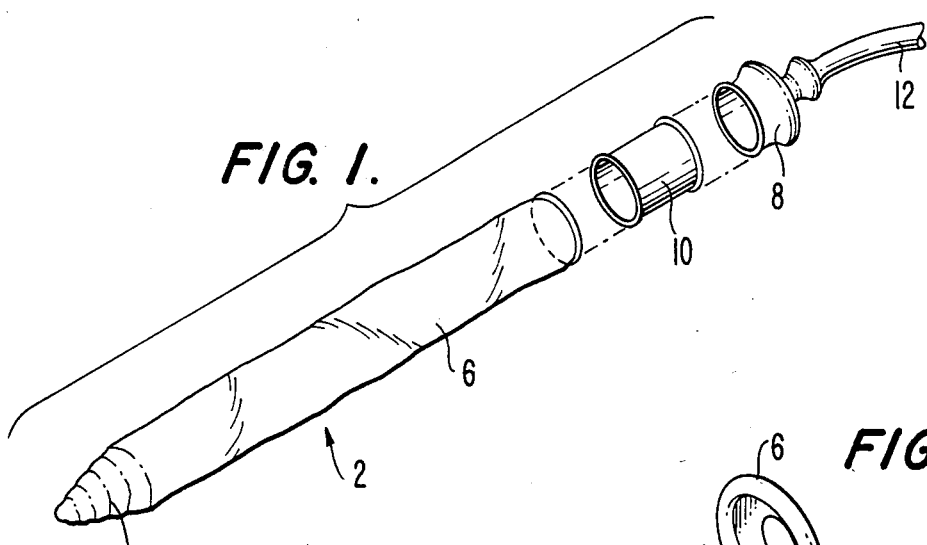
FIG. 1 shows a perspective view of the apparatus of the invention.

FIG. 1 shows a sheath 2 made of an extremely thin, flexible membrane such as 1/64 inch thick natural rubber. The sheath includes a frustoconical, or tapered, portion 4 and a cylindrical, tubular portion 6. The frustoconical portion preferably varies from a smaller diameter of about ½ inch to a larger diameter of about ¾ inch. The frustoconical portion is used for size adjustment, and the taper need not be dramatic if the membrane is adequately resilient. The sheath 2 is preferably connected to a funnel 8 by a connector 10. A discharge tube 12 is in turn connected to the outlet of the funnel 8.

The frustoconical section 4 may be provided with a small hole, but since the preferred method of applying the sheath to a penis involves trimming the frustoconical portion 4 to obtain the proper fit, it is not necessary initially to provide a hole for the passage of urine. The length of the cylindrical section 6 is such as to facilitate connection of the sheath to the connector 10 and to provide a surge volume which will be described below.

Figure 2:
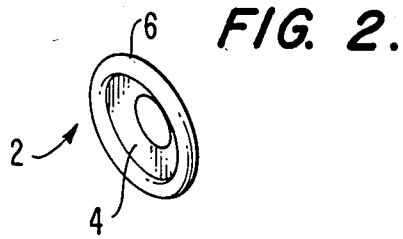
FIG. 2 shows a perspective view of the flexible sheath of the apparatus rolled to a configuration useful for applying the apparatus to a patient.

In the preferred method of applying the sheath 2 to a penis, the sheath is first rolled as shown in FIG. 2.

Figure 3:
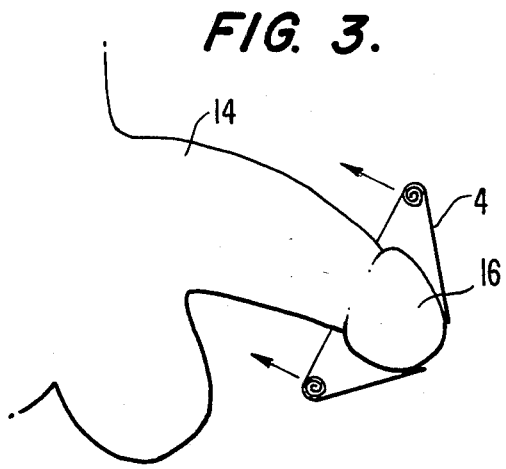
FIG. 3 shows the initial step in applying the apparatus to a patient.

FIG. 3 shows the first step in applying the invention to a penis 14. The glans penis 16 is first coated with lubricant, such as Vaseline or zinc oxide, and the frustoconical portion 4 is forced over the glans penis and onto the base of the penis.

Figure 4:
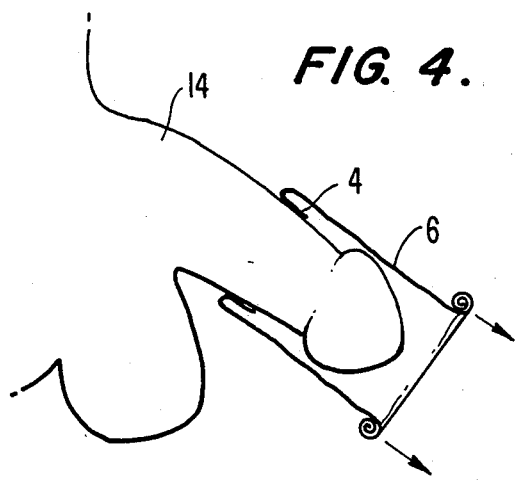
FIG. 4 shows an intermediate step in applying the apparatus to a patient.

FIG. 4 shows the frustoconical portion 4 sealingly engaged with the base of the penis 14. The length of engagement of the frustoconical portion is preferably at least one-fourth of an inch. The cylindrical portion 6 is then folded over the frustoconical portion 4 and unrolled so that it extends outwardly from the patient. It is to be noted that the initial manner of rolling the sheath is such that the cylindrical portion may be easily unrolled after it is folded over the frustoconical portion.

Figure 5:
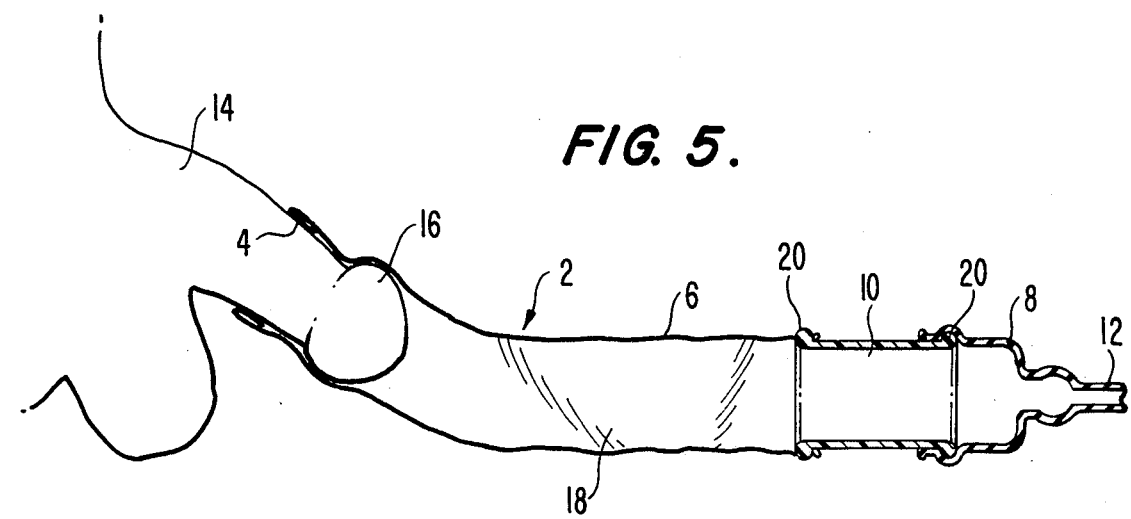
FIG. 5 shows the apparatus applied to a patient wherein the connector and funnel portions are shown in cross section.

FIG. 5 shows the apparatus according to the invention after application to the patient. Because of the natural resiliency of the thin memberane, an extremely good seal is provided between the frustoconical portion 4 and the base of the penis without the application of an additional cuff or collar. The cylindrical portion 6 also provides an additional sealing force in the area engaging the penis.

The portion of the sheath which extends outwardly from the patient provides a surge chamber indicated at 18 in FIG. 5. The volume of this region is extremely variable because of the length of the thin, flexible membrane from which the sheath is made. Urination by the patient does not destroy the seal of the sheath with the penis since any fluid pressure caused by urination will be relieved by expansion of the surge chamber 18 of cylindrical portion 6. Urine then flows into the funnel 8 and discharge tube 12 to a bedside container or other discharge means.

As shown in FIG. 5, the most efficient method of attaching the end of the cylindrical portion 6 which is remote from the frustoconical portion is to provide a lip 20 on the connector 10. It is to be understood that this connection may be made in any manner, such as by providing a collar encircling connector 10 and clamping the cylindrical portion 6 to the connector 10. Similarly, the funnel 8 is shown as engaging a lip 20, but this connection may be made in any desired manner, for example, by the clamp previously referred to or by providing threads on the funnel which engage threads on the connector.

In the method according to the invention, the penis is coated with a lubricant, the frustoconical portion 4 is trimmed to provide a desired diameter, the frustoconical portion 4 is then slid over the glans penis to sealingly engage the base of the penis, and the cylindrical section is folded over the frustoconical section to provide the surge chamber 18 extending outwardly from the patient.

It will be seen that a fundamentally simple and yet quite effective device has been described. This device is not bulky, employs only inexpensive, disposable elements, and has proved to be comfortable for even the most difficult patients.

It is claimed:

1. A method for applying a catheter for directing urine from a male patient comprising
    (a) providing a sheath means of a thin, flexible material and comprising a cylindrical section of a first diameter extending along a major part of the length of said sheath means and a first end section having a second diameter smaller than said first diameter at one end of said cylindrical section,
    (b) pushing said first end section over the glans penis of said patient whereby said first end section engages the base of said penis, and
    (c) folding said cylindrical section back over said said first end section so that a first portion of said cylindrical section forming a urine seal is in contact with said first end section and extending a second portion beyond said glans penis by a distance sufficient to form a surge chamber for collection of urine from said patient.

2. A method according to claim 1 further comprising engaging a second end section of said sheath means with a funnel means, said second end section being remote from said first end section and said funnel means having a larger diameter portion receiving said second end section and a smaller diameter portion for receiving a drain tube, wherein the diameter of said larger diameter portion is larger than the diameter of said second end section when said second end section is not stretched.

3. A method according to claim 2 wherein said step of engaging consists of stretching said second end section over said larger diameter portion.

4. A method according to claim 3 wherein said first end section is frustoconical and said method further comprises the step of adjusting the size of said first end section by removing a part of said first end section.

* * * * *